(12) United States Patent
Porat

(10) Patent No.: US 6,348,057 B1
(45) Date of Patent: Feb. 19, 2002

(54) UMBILICAL CORD CLAMP AND CUTTER

(75) Inventor: Amir Porat, Ganei Yehuda (IL)

(73) Assignee: Kencap Ltd., Ganei Yehuda (IL)

( * ) Notice: Subject to any disclaimer, the term of this patent is extended or adjusted under 35 U.S.C. 154(b) by 0 days.

(21) Appl. No.: 09/640,657

(22) Filed: Aug. 18, 2000

(51) Int. Cl.⁷ .............................................. A61B 17/42
(52) U.S. Cl. ..................................................... 606/120
(58) Field of Search ................................ 606/120, 157, 606/158, 167, 151

(56) References Cited

U.S. PATENT DOCUMENTS

| | | | |
|---|---|---|---|
| 4,312,363 A | * 1/1982 | Rothfuss et al. | 128/774 |
| 4,428,374 A | * 1/1984 | Auburn | 606/120 |
| 5,462,555 A | * 10/1995 | Bolanos et al. | 606/120 |
| 5,584,840 A | * 12/1996 | Ramsey et al. | 606/120 |
| 5,797,922 A | * 8/1998 | Hessel et al. | 606/120 |
| 5,938,666 A | * 8/1999 | Reynolds et al. | 606/120 |
| 5,968,054 A | * 10/1999 | Yeatts, II et al. | 606/120 |

* cited by examiner

*Primary Examiner*—Eduardo C. Robert
(74) *Attorney, Agent, or Firm*—Edward Langer, Pat. Atty.

(57) ABSTRACT

An umbilical cord clamp and cutter assembly with an integral cutting blade. A housing is provided which incorporates a blade, and the housing has removably inserted therein a double clamp in which two clamps are connected by at least one connecting strip. Upon closure of the housing, the double clamp is closed and then the blade becomes engaged and severs the connection between the two clamps. Thus, in one simple one-handed motion, two clamps are closed, and only then the umbilical cord is severed and the clamps are separated in a safe, simple and quick fashion. The motion of closure is similar to other traditional clamps on the market, such that it is easily learned by the user. The two-piece construction simplifies the manufacturing, requiring only the insertion of the double clamp into the housing in a simple motion. The blade is positioned so as to leave minimal tissue after the clamp so as to minimize the opportunity for infection. The housing is constructed so as to remain attached to one clamp, while freeing the other and leaving it attached to the umbilical cord on the infant's side. The housing and its clamp remain attached to the placental side of the umbilical cord, leaving the blade safely separated from the infant. The entire construction may be disposable for ease of use and sterility.

16 Claims, 4 Drawing Sheets

UMBILICAL CORD CLAMP AND CUTTER

FIELD OF THE INVENTION

The present invention relates to a novel umbilical cord clamp and cutter, more particularly to a double clamp with an integral blade for first simultaneously clamping two locations on an umbilical cord and then cutting the cord in one simple action.

BACKGROUND OF THE INVENTION

The process of severing the umbilical cord during the birthing process is a crucial step in separating between the mother and child. Dangers involve possibilities of bleeding, infection and injury by the blade to the infant. In this process the time element is essential.

Current practice involves a three-step process involving the placing of two individual clamps on the umbilical cord at a distance from each other and then cutting between the two clamps. This is a relatively long process and usually requires more than one person to be involved. Additionally, cutting the cord at an indeterminate distance between the two clamps leaves an edge of the cord past the clamp, which is a site prime for infection. The gloved hands applying the clamps on a slippery cord require that the clamps must grasp the cord in a non-slip manner.

There have been a few attempts to make an integrated double clamp and cutter device, most of which have not been found practical enough to come into common use. Those which have actually reached the market are still relatively complicated and difficult to use, and do not necessarily have the safety precautions necessary.

Prior art U.S. Pat. Nos. 5,584,840 and 5,913,862 to Ramsey et al. disclose an umbilical cord cutting and clamping device that includes two clamps held together in a frictional engagement and an integrated blade. The clamp is larger than a standard clamp and different in its operation, such that the user must be trained in its use. As the clamp is closed the blade simultaneously cuts the cord. Because the blade is engaged before the clamp is closed there is a danger that the cut cord will slip out of the clamp. The clamp creates a loop that presses on the cord in such a way that it causes a bend in the cord resulting in additional tissue protruding from the clamp. This is an opening for infection. Additionally, this loop may cause dangerous pulling on the infant's navel. Once the clamp has been closed, the infant-side clamp must then be freed by separating pins from the device, thus requiring an additional complicating step. The device is awkward to use, as it is large and the opening for inserting the cord is narrow. The Ramsey device engages the blade simultaneously with the closing of the clamps, thereby increasing the danger of bleeding.

An additional danger inherent in the prior art double clamps is that there is no clear indication as to how to place the device so that the blade does not end up on the clamp which remains attached to the infant, but rather remains on the mother's side of the cord for discarding with the placenta.

Prior art U.S. Pat. No. 4,781,188 to Collins also discloses an umbilical cord cutting and clamping device that includes two clamps and an integrated blade. The Collins device also engages the blade simultaneously with the closing of the clamps, thereby increasing the danger of bleeding. The device is unwieldly in that it is comprised of multiple parts, which must be separated in a separate step after cutting. The user must be instructed in its use, as it is not similar to the commonly used clamps. The blade cuts the cord in such a way as to leave a significant amount of tissue after the clamp, inviting infection.

U.S. Pat. No. 4,428,374 to Auburn and U.S. Pat. No. 4,026,294 to Mattler disclose awkward solutions to this problem. These devices are equipped with scissor-type handles and require instruction as to their use. Additionally, the Mattler device has a pin which must be removed to separate the clamps, adding another action to an already complicated device (similarly, U.S. Pat. Nos. 5,997,548 and 4,870,965 to Jaahanger).

U.S. Pat. No. 4,716,886 to Schulman discloses a device which is complicated to use and in which an inexperienced user may cut the cord without closing the clamps (similarly, U.S. Pat. No. 4,938,216, also to Schulman and U.S. Pat. No. 5,667,516 to Allen).

U.S. Pat. No. 5,462,555 to Bolanos presents a different approach to an umbilical cord clamp and cutter that comes flat and is folded around the cord. This is large and very complicated to use.

Many of the prior art constructions are larger than a conventional clamp, thus incurring the expense of additional material. Additionally, they are constructed having a number of parts thereby making them difficult to use and dissimilar from the conventional clamp. This makes them undesirable for hospital use, for fear of misuse. (See also U.S. Pat. Nos. 5,190,556 and 5,520,699 to Hessel, U.S. Pat. No. 5,575,795 to Andersen, U.S. Pat. No. 4,856,517 to Collins and U.S. Pat. No. 5,676,672 to Watson et al.)

Therefore, it would be desirable to provide an economical double clamp that is easily assembled from two parts, closes and separates in an easy one-handed motion, first clamping the cord and then cutting through the cord without leaving a significant amount of tissue after the clamp.

SUMMARY OF THE INVENTION

Accordingly, it is a broad object of the present invention to overcome the problems of the prior art and provide an umbilical cord clamp and cutter assembly featuring simple one-handed cutting and clamping motion, to leave minimal tissue after the clamp so as to minimize the opportunity for infection.

In accordance with a preferred embodiment of the present invention, there is provided an umbilical cord clamp and cutter assembly comprising:

a first clamp comprising a first upper arm, a first lower arm, a first flexible region and a first closing mechanism for attaching to the infant side of an umbilical cord;

a second clamp comprising a second upper arm, a second lower arm, a second flexible region and a second closing mechanism for attaching to the placental side of the umbilical cord, the first and second clamps being connected in a side-by-side relationship and having between them at least one connecting strip; and an outer housing comprising a third upper arm, a third lower arm, a third flexible region and a third closing mechanism, and having perpendicularly attached to the third upper arm, a cutting device extending downwardly in the direction of the third lower arm, the outer housing being formed so as to enclose the first and second clamps, such that upon closing the housing, the first and second clamps close around the umbilical cord, the cutting device cuts through the cord and the at least one connecting strip, and the second clamp remains enclosed by the housing, while the first clamp becomes separated from the second clamp, housing and cutting device.

Additionally, there is provided a method of clamping and cutting and umbilical cord, the method comprising the steps of:

providing an umbilical cord clamp and cutter assembly, comprising:

a first clamp comprising a first upper arm, a first lower arm, a first flexible region and a first closing mechanism for attaching to the infant side of an umbilical cord;

a second clamp comprising a second upper arm, a second lower arm, a second flexible region and a second closing mechanism for attaching to the placental side of an umbilical cord, the first and second clamps being connected in a side-by-side relationship and having between them at least one connecting strip; and an outer housing comprising a third upper arm, a third lower arm, a third flexible region and a third closing mechanism, and having perpendicularly attached to the third upper arm, a cutting device extending downwardly in the direction of the third lower arm, the outer housing being formed so as to enclose the first and second clamps;

inserting an umbilical cord into the umbilical cord clamp and cutter assembly; and pressing upon the upper arm of the housing in a closing motion, such that in a first part of said closing motion the first and second clamps are closed, and in a continuation of said closing motion the cutting device is engaged, cutting the cord and the at least one connecting strip.

In accordance with a preferred embodiment of the present invention there is provided an umbilical cord clamp with an integral cutting blade. A housing is provided which incorporates a blade. Removably insertable in the housing is a double clamp in which two clamps are connected by at least one connecting strip. Upon closure of the housing, the double clamp is closed and then the blade becomes engaged and severs the connection between the two clamps. Thus, in one simple one-handed motion, two clamps are closed, and only then the umbilical cord is severed and the clamps are separated in a safe, simple and quick fashion.

The motion of closure is similar to other traditional clamps on the market, such that it is easily learned by the user. The two-piece construction simplifies the manufacturing, requiring only the insertion of the double clamp into the housing in a simple motion. The blade is positioned so as to leave minimal tissue after the clamp so as to minimize the opportunity for infection. The housing is constructed so as to remain attached to one clamp, while freeing the other and leaving it attached to the umbilical cord on the infant's side. The housing and its clamp remain attached to the placental side of the umbilical cord, leaving the blade safely separated from the infant. The blade is positioned so as to leave any rough edges on the clamp connected to the placenta, so as to separate them from the infant. The entire construction may be disposable for ease of use and sterility.

The clamps are provided with a ribbed area on the interior of both the upper and lower arms for non-slip gripping of the umbilical cord. A stop mechanism is provided to assure that the cord is not inserted too far. The closing mechanism of the clamps may be provided, by way of example, by a tooth extending from the front of the lower arm of the clamp, engaging a ridged indentation in the upper arm. A flexible region connects the upper and lower arms. The two clamps are attached by at least one connecting strip.

The housing is provided as a lower arm and an upper arm, connected by a flexible region. A closing mechanism is provided, by way of example, in the form of an inwardly facing ledge, which, upon closure of the housing engages a protruding lip on the lower arm. A blade descends perpendicularly from the upper arm. The lower arm is formed with a ridge such that when the double clamp is inserted in the housing, the ridge inserts between the two clamps in their attached form and assures that the clamps do not slip. The inwardly facing ledge additionally has formed on either side of the ledge a pin.

Upon closure of the housing, the pins press on a platform formed in the upper arm of the clamps, so as to close the mechanisms on the clamps, and then the pins slide through a ridged indentation in the platform allowing any connecting strips between the upper arms to be cut before the blade cuts the cord. The changing of the angle between the upper and lower arms aligns the closing mechanism. The cord is then cut, and the blade then cuts any connecting strips between the lower arms, freeing one clamp to separate off with the infant. The connecting strips are cut close to the freed clamp so not to leave any sharp edges to scratch the infant. The housing remains with the clamp attached to the placenta.

Other features and advantages of the invention will become apparent from the following drawings and descriptions.

BRIEF DESCRIPTION OF THE DRAWINGS

For a better understanding of the invention with regard to the embodiments thereof, reference is made to the accompanying drawings, in which like numerals designate corresponding elements or sections throughout and in which.

DETAILED DESCRIPTION OF A PREFERRED EMBODIMENT

Figure 1:
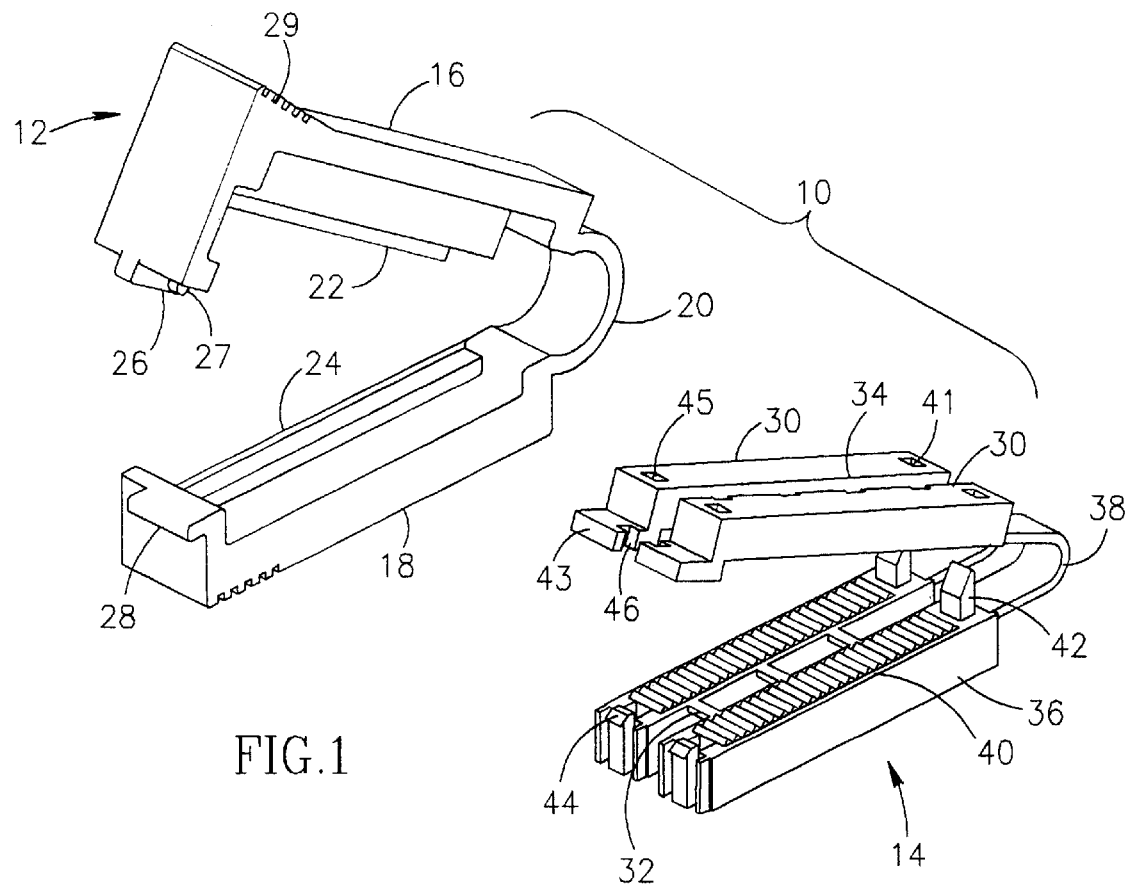
FIG. 1 is a perspective view of a preferred embodiment of an umbilical cord clamp and cutter assembly, featuring a housing and double clamp.

Referring now to FIG. 1, there is shown a preferred embodiment of an umbilical cord clamp and cutter assembly 10, constructed and operated in accordance with the principles of the present invention. Assembly 10 comprises a housing 12 and double clamp 14. Housing 12 comprises upper arm 16 and lower arm 18, which are connected by a flexible region 20. Extending from upper arm 16 in a perpendicular fashion is blade 22. Lower arm 18 is provided with ridge 24 for securing double clamp 14 in place. Housing 12 has a closing mechanism provided as, by way of example, inwardly facing ledge 26, which, upon closure of the housing engages protruding lip 28 on the lower arm. Inwardly facing ledge 26 has formed on either side pin 27. A non-slip grip 29 is provided to assure a smooth closing motion.

Double clamp 14 is provided as two clamps 30 connected by at least one connecting strip 32. Clamps 30 are comprised of upper arms 34 and lower arms 36 with a flexible region 38 between the upper and lower arms. Clamps 30 are provided with a ribbed area 40 on both the upper arms 34 and lower arms 36 for non-slip gripping of the umbilical cord. A stop mechanism 42 is provided to assure that the cord is not inserted too far. Stop mechanism 42 additionally serves to add stability and positioning to clamp 30 when it is in a closed state by inserting into hole 41 in upper arm 34. Platform 43, along with ledge 26 and pins 27 create a mechanism which allows for closing of clamp 30, before engagement of blade 22. The closing mechanism of the clamps may be provided, by way of example, by a hooked tooth 44 extending upwardly from the front of the lower arm of the clamp, engaging hole 45 in upper arm 34.

Figure 2:
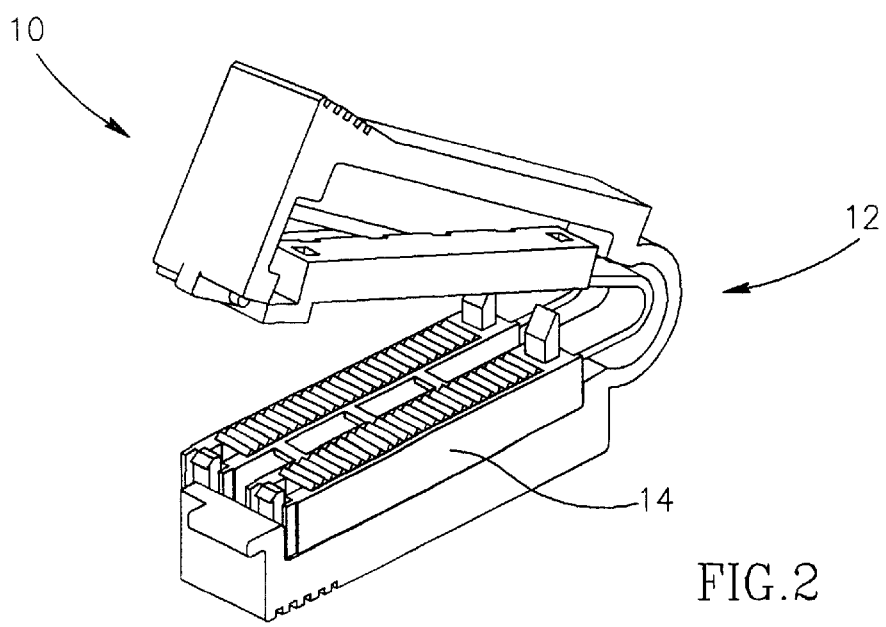
FIG. 2 is a perspective view of the assembly of the double clamp inserted in the housing.

As shown in FIG. 2, double clamp 14 is inserted in housing 12 such that ridge 24 secures it in place. Double clamp 14 sits in housing 12 in an asymmetric fashion, such that one of clamps 30 is more visible than the other. This provides a clear indication to the user which side to place facing the placenta and which side facing the infant. Additionally, the word "baby" or "infant" or a similarly indicative word may be formed on clamp 30 or on housing 12 so as to indicate which side is to be attached to the infant and which to the placenta. Clamps 30 may be provided in different colors for indication of which side is designated for the placenta and which for the infant.

Figure 3:
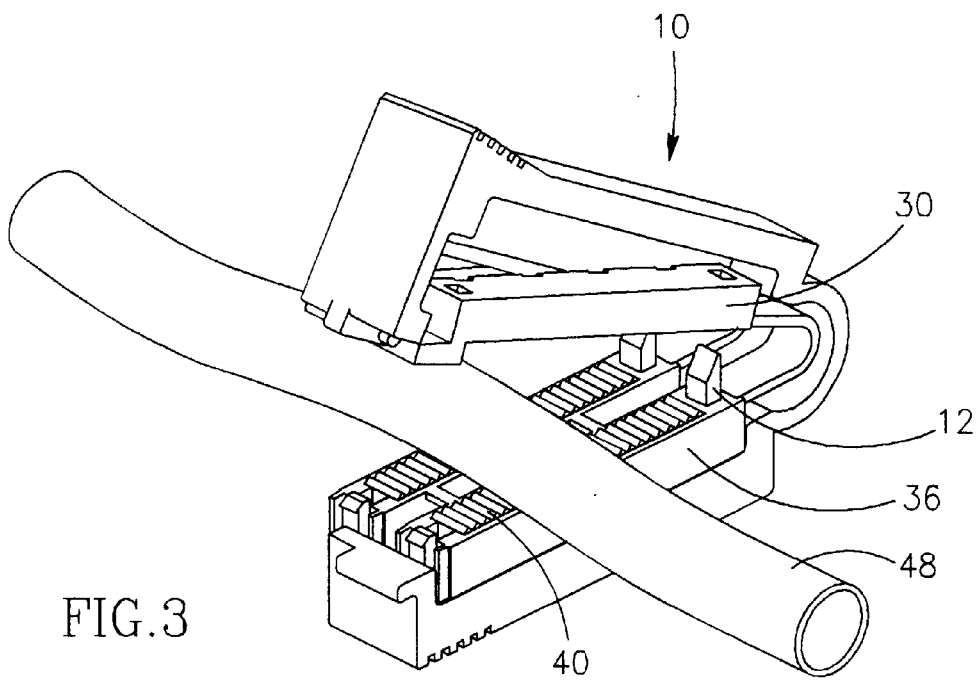
FIG. 3 shows the cord being inserted into the assembly.

In FIG. 3, assembly 10 is shown with cord 48 inserted between upper arms 34 and lower arms 36. Ribbed areas 40 prevent slippage of cord 48 and stop mechanisms 42 prevent cord 48 from entering the assembly too far.

Figure 4:
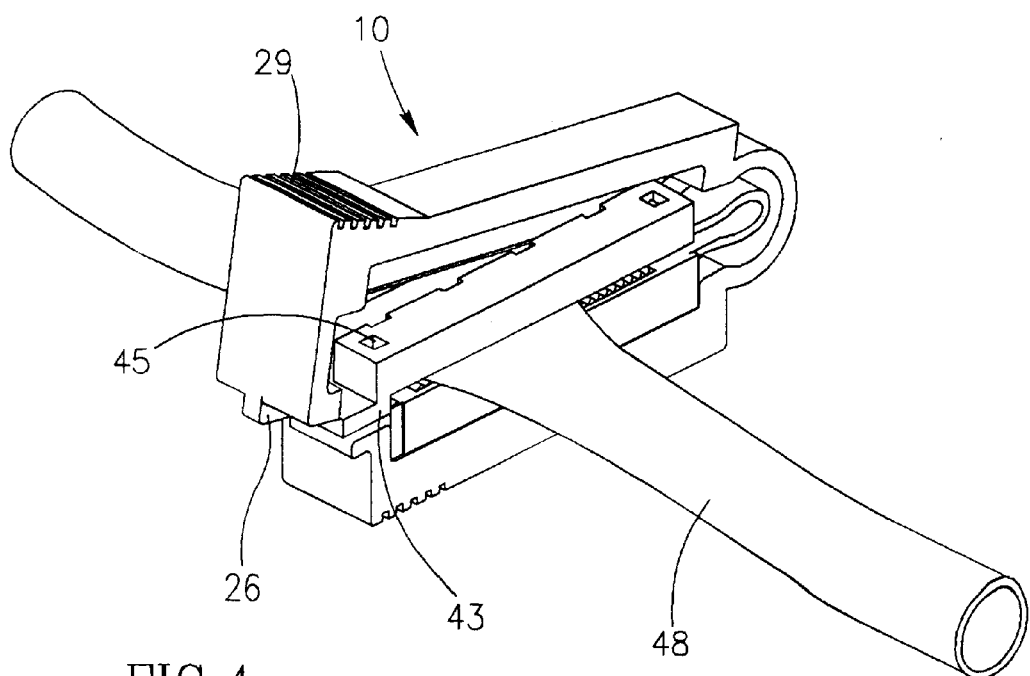
FIG. 4 shows the first stage of closing the clamps of the assembly.

Referring now to FIG. 4, assembly 10 is shown after double clamp 14 has been closed by the closing motion of housing 12. As inwardly facing ledge 26 descends, it first presses on platforms 43 closing both clamps 30, by causing hooked tooth 44 to engage in hole 45. For further secure alignment, stop mechanism 42 engages in hole 41. The changing of the angle between upper arm 34 and lower arm 36 aligns the closing mechanism. Blade 22 is not yet engaged.

Figure 5:
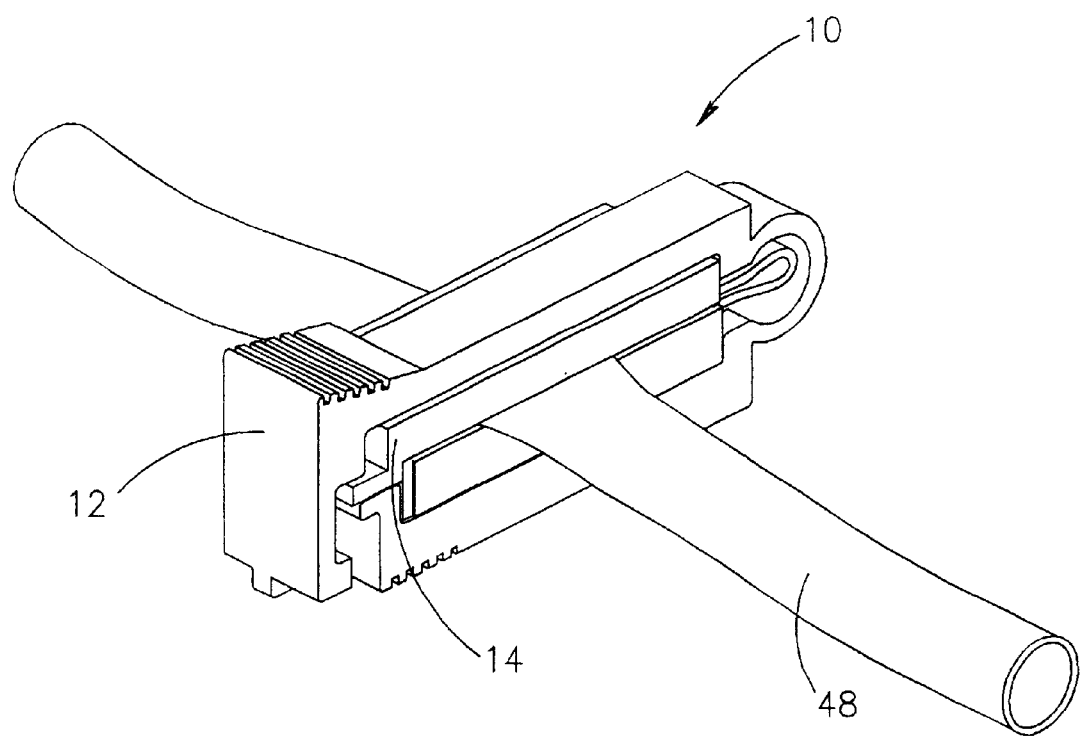
FIG. 5 shows the second stage of closing of the assembly.

In a continuation of the descent, pins 27 on inwardly facing ledge 26 slide through ridged indentations 46 on platforms 43 allowing ledge 26 to engage protruding lip 28, engaging blade 22, resulting in a closed assembly as shown in FIG. 5.

Figure 6:
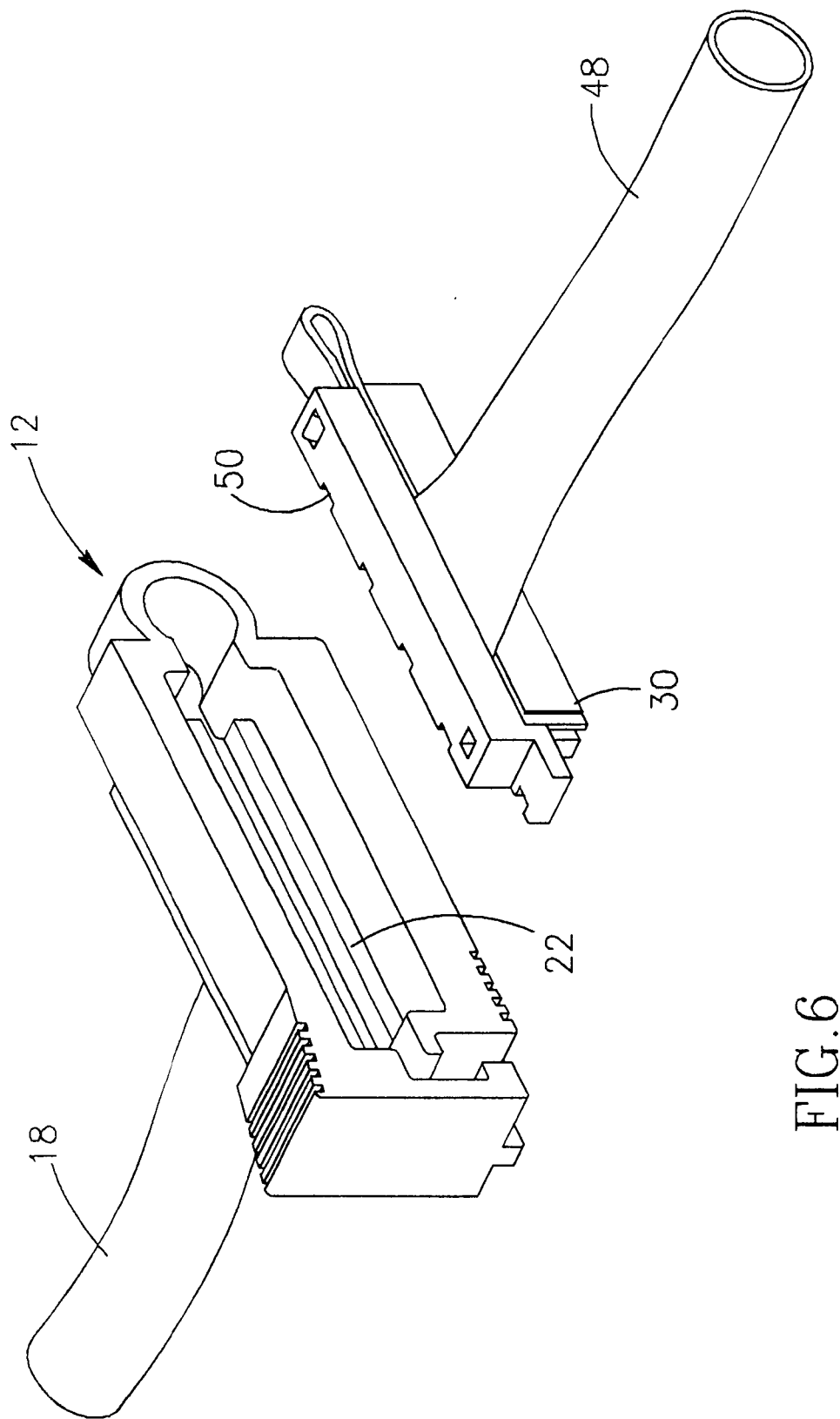
FIG. 6 shows the assembly after the clamps have been separated and the cord has been cut.

As seen in FIG. 6, this further closing motion of housing 12 results in the activation of blade 22, cutting through connecting strips 32 between the upper arms 34 of clamps 30, then cutting through cord 48, and finally cutting through any connecting strips between lower arms 36 of clamps 30, freeing a separated single clamp 30. Cord 48 is cut in such a fashion that it is flush with the clamp 30 that remains attached to the infant. Thus, chances for infection are minimized as necrotic tissue is minimized.

Blade 22 cuts connecting strips 32 in such a way that any rough edges which are formed remain on the placenta clamp. Housing 12 is locked shut with the clamp 30 that is connected to the placenta within. Indentations 50 on infant-side clamp 30 allow the blade attachment to pass through, so as not to distance blade 22 from clamp 30, thus insuring that blade 22 cuts evenly with the edge of clamp 30 leaving a minimum of tissue. Thus, clamp 30 that is attached to the infant is left with no rough edges and no blade and a minimum of excess tissue, providing a safe clamp for the infant.

In summary, the clamp and cutter assembly of the present invention provides a simply constructed, easy to use device which is disposable and minimizes infection.

Having described the invention with regard to certain specific embodiments thereof, it is to be understood that the description is not meant as a limitation, since further modifications may now suggest themselves to those skilled in the art, and it is intended to cover such modifications as fall within the scope of the appended claims.

I claim:

1. An umbilical cord clamp and cutter assembly, comprising:

a first clamp comprising a first upper ann, a first lower arm, a first flexible region, a first stop mechanism wherein said first upper arm is formed with a first hole therein and said first lower arm is provided with an upwardly extending tooth for engaging said first hole in said first upper arm, and a first closing mechanism for closing said first clamp so as to attach to an infant side of the umbilical cord;

a second clamp comprising a second upper arm, a second lower arm, a second flexible region, a second stop mechanism wherein said second upper arm is formed with a second hole therein and said second lower arm is provided with an upwardly extending tooth for engaging said second hole in said second upper arm, and a second closing mechanism for closing said second clamp so as to attach to a placental side of the umbilical cord, said first and second clamp being connected in a side-by-side relationship and having between them at least one connecting strip; and an outer housing comprising an indication in which direction to attach the assembly, a third upper ann, a third lower arm, a third flexible region and a third closing mechanism, and having perpendicularly attached to said third upper arm, a cutting device extending downwardly toward said third lower arm, said outer housing being formed so as to enclose said first and second clamps, wherein upon closing said housing said third closing mechanism holds said housing closed, such that upon closing of said housing, said first and second clamps close around the umbilical cord, said cutting device cuts through file cord and said at least one connecting strip, and said second clamp remains enclosed by said housing, while said first clamp becomes separated from said second clamp, said housing and said cutting device.

2. The assembly of claim 1 further comprising a ribbed area on said first and second upper and lower arms for preventing slippage of the cord.

3. The assembly of claim 1 further comprising a stop mechanism on said first and second clamps for preventing the cord from being inserted too far and for strengthening said first and second clamps upon closing.

4. The assembly of claim 1 wherein said third closing mechanism works in two stages, a first stage in which said first and second clamps are closed, and a second stage in which the cord is cut and said first and second clamps are separated.

5. The assembly of claim 1 wherein said first and second upper arms are formed with a second hole therein and wherein said first and second closing mechanisms are provided as a hooked tooth extending upwardly from a front end of said lower arms of said first and second clamps, for engaging a second hole in said upper arms of said first and second clamps.

6. The assembly of claim 1 wherein said third closing mechanism is provided as an inwardly facing ledge on said third upper arm and a protruding lip on said third lower arm, upon closing said housing said ledge engages said lip to hold said housing closed.

7. The assembly of claim 6 wherein said inwardly facing ledge is further provided with at least one pin, and said first and second upper arms are further provided with a platform having formed therein a ridged indentation, such that upon closing of said housing around said first and second clamps, said at least one pin presses on said platform, closing said first and second clamps, and upon further pressure said at least one pins slides through said ridged indentation, while an angle created by said third upper and said third lower arm becomes smaller allowing said ledge to engage said lip so as to hold said housing closed.

8. The assembly of claim 1 wherein said housing is constructed asymmetrically so as to indicate in which direction to attach the assembly.

9. The assembly of claim 1 wherein said assembly is provided with a legibleindication of a direction in which to attach the assembly with respect to the infant and placental sides of the cord.

10. The assembly of claim 1 wherein said housing further comprises a non-slip grip.

11. The assembly of claim 1 wherein said cutting device descends in close proximity to said first clamp cutting said at least one connecting strip such that said at least one connecting strip remains attached to said second clamp.

12. The assembly of claim 11 wherein said first clamp is formed with indentations to allow an attachment mechanism for said cutting device to pass through, such that said cutting device cuts leaving a minimal amount of tissue past said first clamp.

13. The assembly of claim 1 wherein said first and second clamps and said at least one connecting strip comprise a double clamp.

14. The assembly of claim 13 wherein said assembly is provided as a two-part construction comprised of said housing and said double clamp, said cutting device separating said two-part construction into three parts said three parts comprising said housing, said first clamp and said second clamp.

15. A method of clamping and cutting an umbilical cord, said method comprising the steps of:

providing an umbilical cord clamp and cutter assembly, comprising:

a first clamp comprising a first upper arm, a first lower arm, a first flexible region, a first stop mechanism wherein said first upper arm is formed with a first hole therein and said first lower arm is provided with an upwardly extending tooth for engaging said first hole in said first upper arm, and a first closing mechanism for attaching to an infant side of an umbilical cord;

a second clamp comprising a second upper arm, a second lower arm, a second flexible region, a second stop mechanism wherein said second upper arm is formed with a second hole therein and said second lower arm is provided with an upwardly extending tooth for engaging said second hole in said second upper arm, and a second closing mechanism for attaching to a placental side of the umbilical cord, said first and second clamp being connected in a side-by-side relationship and having between them at least one connecting strip; and an outer housing comprising a third upper arm, a third lower arm, a third flexible region and a third closing mechanism, and having perpendicularly attached to said third upper arm, a cutting device extending downwardly toward said third lower arm, said outer housing being formed so as to enclose said first and second clamps, inserting an umbilical cord into said umbilical cord clamp and cutter assembly; and pressing upon said upper arm of said housing in a closing motion, such that in a first part of said closing motion said first and second clamps are closed, and in a continuation of said closing motion said cutting device is engaged, cutting the cord and said at least one connecting strip.

16. An umbilical cord clamp and cutter assembly, comprising:

a first clamp means for attaching to an infant side of the umbilical cord;

a second clamp means for attaching to a placental side of the umbilical cord, said first and second clamp means being connected in a side-by-side relationship and having between them at least one connecting strip; and an outer housing being formed so as to enclose said first and second clamps, and having attached thereto, a cutting device extending downwardly such that upon closing of said housing, said first and second clamp means close around the umbilical cord, said cutting device cuts through the cord and said at least one connecting strip, and said second clamp remains enclosed by said housing, while said first clamp becomes separated from said second clamp, said housing and said cutting device, wherein said housing further comprises means for indicating in which direction to attach the assembly with respect to the infant and placental sides of the cord.

* * * * *